United States Patent
Huang et al.

(10) Patent No.: US 11,516,979 B2
(45) Date of Patent: Dec. 6, 2022

(54) METHOD FOR CONDUCTING HIGH-THROUGHPUT AND DIRECTED MUTAGENESIS FOR SUGARCANE RESISTANCE TO GLYPHOSATE BY PLASMA

(71) Applicant: GUANGDONG PROVINCIAL BIOENGINEERING INSTITUTE (GUANGZHOU SUGARCANE INDUSTRY RESEARCH INSTITUTE), Guangzhou (CN)

(72) Inventors: Zhongxing Huang, Guangzhou (CN); Donglei Sun, Guangzhou (CN); Yuanxian Xu, Guangzhou (CN); Huiyi He, Guangzhou (CN); Lina Fan, Guangzhou (CN); Fangye Lao, Guangzhou (CN); Qiuping Ling, Guangzhou (CN); Yuxing An, Guangzhou (CN)

(73) Assignee: INSTITUTE OF NANFAN & SEED INDUSTRY, GUANGDONG ACADEMY OF SCIENCES, Guangzhou (CN)

( * ) Notice: Subject to any disclaimer, the term of this patent is extended or adjusted under 35 U.S.C. 154(b) by 250 days.

(21) Appl. No.: 16/315,016

(22) PCT Filed: Oct. 27, 2017

(86) PCT No.: PCT/CN2017/107910
§ 371 (c)(1),
(2) Date: Jan. 3, 2019

(87) PCT Pub. No.: WO2019/061621
PCT Pub. Date: Apr. 4, 2019

(65) Prior Publication Data
US 2021/0345571 A1    Nov. 11, 2021

(30) Foreign Application Priority Data
Sep. 26, 2017    (CN) .......................... 201710880009.X

(51) Int. Cl.
*A01H 1/06* (2006.01)
*A01H 1/00* (2006.01)
*A01H 4/00* (2006.01)

(52) U.S. Cl.
CPC ............. *A01H 1/06* (2013.01); *A01H 1/1235* (2021.01); *A01H 4/008* (2013.01)

(58) Field of Classification Search
None
See application file for complete search history.

(56) References Cited

FOREIGN PATENT DOCUMENTS

| | | |
|---|---|---|
| CN | 102911965 A | 2/2013 |
| CN | 104403974 A | 3/2015 |
| CN | 105039389 A | 11/2015 |
| CN | 204874543 U | 12/2015 |

OTHER PUBLICATIONS

Ottenheim, C., Nawrath, M. & Wu, J.C. Microbial mutagenesis by atmospheric and room-temperature plasma (ARTP): the latest development. Bioresour. Bioprocess. 5, 12 (2018). https://doi.org/10.1186/s40643-018-0200-1.*
The International Search Report for PCT/CN2017/107910, dated Jun. 27, 2018.
Zhang, et al., "Atmospheric and Room Temperature Plasma (ARTP) as a New Powerful Mutagenesis Tool", Applied Microbiology and Biotechnology, First Online: Apr. 27, 2014, Beijing, People's Republic of China.

* cited by examiner

*Primary Examiner* — Phuong T Bui
(74) *Attorney, Agent, or Firm* — M&B IP Analysts, LLC

(57) ABSTRACT

The present invention relates to a method for conducting high-throughput and directed mutagenesis for sugarcane resistance to glyphosate by plasma. The method is as follows: sugarcane embryonic calli are irradiated by a plasma instrument under a sterile condition for mutagenesis, wherein the mutagenesis power is 140~200 W, the discharging distance is 35~45 mm, the mutagenesis time is 110~140 s and the protective gas is nitrogen; buffering culture, moderate/high concentration of glyphosate stress screening, differentiation into seedlings, glyphosate stress screening of bottle seedlings and stress screening via spraying glyphosate on the leave surfaces of potted plants are conducted for the treated calli. The present invention has the advantages of safe operation, simplicity, practicability, high handling capacity, low contamination, and due to implementation of directed stress screening, high screening efficiency, decreased subsequent screening workload and visual identification of resistant mutant strains.

8 Claims, 2 Drawing Sheets

METHOD FOR CONDUCTING HIGH-THROUGHPUT AND DIRECTED MUTAGENESIS FOR SUGARCANE RESISTANCE TO GLYPHOSATE BY PLASMA

CROSS-REFERENCE TO RELATED APPLICATIONS

This application is the United States National Stage entry under 35 U.S.C. 371 of PCT/CN2017/107910 filed on Oct. 27, 2017, which in turn claims the priority of Chinese patent application No. 201710880009.X entitled "method for conducting high-throughput and directed mutagenesis for sugarcane resistance to glyphosate by plasma" filed on Sep. 26, 2017, both of which are hereby incorporated by reference in their entireties.

FIELD OF THE INVENTION

The present invention relates to a method for conducting high-throughput and directed mutagenesis for sugarcane resistance to glyphosate by plasma.

BACKGROUND OF THE INVENTION

Sugarcane is an important sugar crop in China, and cane sugar accounts for more than 90% of the sugar yield in China. The development of sucrose industry largely depends on the improvement of sugarcane varieties, since superior varieties take up 60% of contribution to the technical progress of sucrose production and are the core technology for Chinese sucrose industry in its sustainable development and in enhancement of ability of its international competitiveness. There are more or less disadvantages during the production process of superior varieties, for example, weak drought resistance or no resistance to glyphosate. Sugarcane mutation breeding is a rapid way to improve cultivated sugarcane varieties, which improves the undiversified structure of the sugarcane variety in China. An important point in the sugarcane mutation breeding is to reduce callus contamination, and the invention of irradiating sugarcane callus with low-energy plasma beam provides a good environmental condition for the sugarcane callus, thus ensuring the smooth implementation of sugarcane mutation breeding.

In the earlier stage, the comparatively traditional mutagenesis for sugarcane callus is mainly conducted using a chemical mutagen or a Co60-r ray. For the callus chemical mutagenesis, on one hand, the chemical mutagen has carcinogenic risks to human body; on the other hand, it is likely to cause contamination during operation; and moreover, due to the limited handling capacity, it cannot satisfy test demands. And for the Co60-r ray mutagenesis, the method has good effects, but requires a special place and special protections as well as high operation costs. In a microbial culturing process, operators generally in the past stuffed a slant medium test tube with cotton near the opening of the tube and placed the tube in a plasma machine for mutagenesis, thus avoiding contamination. Although such method has a good effect in preventing microorganisms, some disadvantages, such as too little space, inconvenient operation and low handling capacity, exist.

SUMMARY OF THE INVENTION

To solve the existing problems above, a high-throughput mutagenesis method for sugarcane embryonic callus is provided in this present invention for the first time, which prevents the problem of cancer risks to human caused by chemical mutagen, enabling technicians to work without worries. Moreover, the method not only solves the problem that the sugarcane callus is easily contaminated traditionally, but also adapts to the mutagenesis demand for mass sugarcane calli, solving the problem of inconvenient operation and low handling capacity with the test tube slant medium. Meanwhile, the invention shows an obvious difference in mutagenic effectiveness and may determine the mutagenesis time based on the survival rate of the embryonic calli rapidly, thus improving mutation breeding efficiency through directed stress screening, with its mutagenesis rate up to 2.50%-2.77%.

An object of this present invention is to provide a method for conducting high-throughput and directed mutagenesis for sugarcane resistance to glyphosate by plasma.

The technical solution adopted in this present invention is described as follows:

a method for conducting high-throughput and directed mutagenesis for sugarcane resistance to glyphosate by plasma, comprising the following steps:

(1) sugarcane embryonic calli are irradiated by a plasma instrument under a sterile condition for mutagenesis, wherein the mutagenesis power is 140~200 W, the discharging distance is 35~45 mm, the mutagenesis time is 110~140 s and the protective gas is nitrogen;

(2) the sugarcane embryonic calli after mutagenesis in the above step are inoculated to a solid medium CM2 and sealed by a film for buffering culture for 8~10 days;

the medium CM2 contains: a MS medium, 1.2~1.7 $\mu mol \cdot L^{-1}$ of 2,4-D, 28~32 $g \cdot L^{-1}$ of sucrose and 7.5~8.5 $g \cdot L^{-1}$ of agar, and the pH of the medium is 6.0~6.4;

(3) after buffering culture, the sugarcane calli are in turn inoculated to a solid medium CM3 containing 1.2~1.7 $\mu mol \cdot L^{-1}$ of glyphosate and to a solid medium CM3 containing 2.2~2.7 $\mu mol \cdot L^{-1}$ of glyphosate, then sealed by a film for screening culture for 8~10 days respectively;

the medium CM3 contains: a MS medium, 28~32 $g \cdot L^{-1}$ of sucrose and 7.5~8.5 $g \cdot L^{-1}$ of agar, and the pH of the medium is 6.0~6.4;

(4) the embryonic calli survived in the above step are transferred to a solid differentiation medium CM4 for cultivation till seedlings emerge, then subculture is conducted once;

the medium CM4 contains: a MS medium, 0.4~0.6 $\mu mol \cdot L^{-1}$ of NAA, 0.8~1.2 $\mu mol \cdot L^{-1}$ of Kt, 48~52 $g \cdot L^{-1}$ of sucrose, 7.5~8.5 $g \cdot L^{-1}$ of agar, and the pH of the medium is 6.0~6.4;

(5) after growing to 20 mm-30 mm, the seedlings in the above step are transferred to a CM5 for screening culture;

the medium CM5 contains: a MS medium, 4.8~5.2 $\mu mol \cdot L^{-1}$ of glyphosate, 28~32 $g \cdot L^{-1}$ of sucrose, 8 $g \cdot L^{-1}$ of agar, and the pH of the medium is 6.0~6.4;

(6) the seedlings survived in the above step are inoculated to a CM4 for proliferation culture, and then transferred to a CM6 for root-growth culture and seedling hardening, then transplanted to a seedbed, and after growing to 100 mm~150 mm, the seedlings are screened by spraying 4.8~5.2 $\mu mol \cdot L^{-1}$ of glyphosate, the survived seedlings are glyphosate-resistant strains;

the medium CM6 contains: ½MS medium, 0.4~0.6 $\mu mol \cdot L^{-1}$ of NAA, 1.8~2.2 $\mu mol \cdot L^{-1}$ of 6-BA, 28~32 $g \cdot L^{-1}$ of sucrose, and the pH of the medium is 6.0~6.4.

Further preferably, in step (1), the mutagenesis power is 140 W, the irradiation distance is 40 mm and the mutagenesis time is 120 s.

Further preferably, in step (1), the nitrogen flow is 1.0~1.4 L/min.

Further preferably, the plasma instrument is an HPD-280 plasma machine produced by Nanjing Suman Electronics Co., Ltd.

Further preferably, the plasma instrument is sterilized before use, wherein a vessel containing 28~32% of $H_2O_2$ solution is put in a process chamber for diffuse sterilization by vacuum.

Further preferably, in step (1), the sugarcane embryonic calli are obtained after 2-3 rounds of subculture.

Further preferably, in step (1), the preparation method of the sugarcane embryonic calli is as follows: cutting the tail end of a robust sugarcane plant after its stalk grows out, stripping outer leaves, sterilizing it by alcohol under a sterile condition, and cutting off leaves on the outer layer and both ends thereof, keeping tender leaves 10 mm-50 mm above the growing point and cutting the tender leaves into thin slices, inoculating the slices to a CM1 medium for culturing at 26° C.~28° C. in dark to induce the formation of calli, then conducting subculture for 1-2 times with a CM1 medium, thus producing the sugarcane embryonic calli.

Further preferably, the medium CM1 is a MS medium containing 1.8~2.2 $\mu mol \cdot L^{-1}$ of 2,4-D, 28~32 $g \cdot L^{-1}$ of sucrose and 7.5~8.5 $g \cdot L^{-1}$ of agar, and the pH of the medium is 6.0~6.4.

Further preferably, in step (5), the screening culture is continued for 26~30 days.

Furthermore, in step (6), the proliferation culture is continued for 28~32 days.

Advantageous effects of the present invention are described for example as follows:

(1) the invention is simple in operation and low in contamination which brings convenience for sugarcane callus mutagenesis;

(2) the invention solves the problem of inconvenient operation and low handling capacity with the test tube slant medium, and may achieve mass mutagenesis; it shows an obvious difference in its mutagenic effectiveness and may determine the mutagenesis treatment time based on the survival rate of the embryonic calli rapidly;

(3) the invention has high mutagenesis efficiency which may be up to 2.50%-2.77%;

(4) in the present invention, the directed stress screening may be conducted to reduce the subsequent screening workload.

(5) resistance of the mutant strains may be identified visually.

DETAILED DESCRIPTION OF THE EMBODIMENTS

Figure 1:
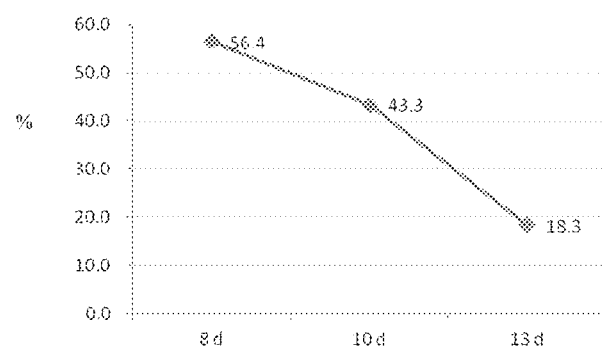
FIG. 1 shows the influence of number of days of buffering culture after plasma mutagenesis on the survival rate of the sugarcane embryonic calli.

A method for conducting high-throughput and directed mutagenesis for sugarcane resistance to glyphosate by plasma is provided, comprising the following steps:

(1) sugarcane embryonic calli are irradiated by a plasma instrument under a sterile condition for mutagenesis, wherein the mutagenesis power is 140~200 W, the discharging distance is 35~45 mm, the mutagenesis time is 110~140 s and the protective gas is nitrogen;

(2) the sugarcane embryonic calli treated by mutagenesis in the above step are inoculated to a solid medium CM2 and sealed by a film for buffering culture for 8~10 days;

the medium CM2 contains: a MS medium, 1.2~1.7 $\mu mol \cdot L^{-1}$ of 2,4-D, 28~32 $g \cdot L^{-1}$ of sucrose and 7.5~8.5 $g \cdot L^{-1}$ of agar, and the pH of the medium is 6.0~6.4;

(3) after buffering culture, the sugarcane calli are in turn inoculated to a solid medium CM3 containing 1.2~1.7 $\mu mol \cdot L^{-1}$ of glyphosate and to a solid medium CM3 containing 2.2~2.7 $\mu mol \cdot L^{-1}$ of glyphosate, then sealed by a film for screening culture for 8~10 days;

the medium CM3 contains: a MS medium, 28~32 $g \cdot L^{-1}$ of sucrose and 7.5~8.5 $g \cdot L^{-1}$ of agar, and the pH of the medium is 6.0~6.4;

(4) the embryonic calli survived in the above step are transferred to a solid differentiation medium CM4 for cultivation and are subcultured once after seedling emergence;

the medium CM4 contains: a MS medium, 0.4~0.6 $\mu mol \cdot L^{-1}$ of NAA, 0.8~1.2 $\mu mol \cdot L^{-1}$ of Kt, 48~52 $g \cdot L^{-1}$ of sucrose and 7.5~8.5 $g \cdot L^{-1}$ of agar, and the pH of the medium is 6.0~6.4;

(5) after growing to 20 mm-30 mm, the seedlings in the above step are transferred to a CM5 for screening culture;

the medium CM5 contains: a MS medium, 4.8~5.2 $\mu mol \cdot L^{-1}$ of glyphosate, 28~32 $g \cdot L^{-1}$ of sucrose, 8 $g \cdot L^{-1}$ of agar, and the pH of the medium is 6.0~6.4;

(6) the seedlings survived in the above step are inoculated to a CM4 for proliferation culture, and then transferred to a CM6 for root-growth culture and seedling hardening, then transplanted to a seedbed, and after growing to 100 mm~150 mm, the seedlings are screened by spraying 4.8~5.2 $\mu mol \cdot L^{-1}$ of glyphosate, the survived seedlings are glyphosate-resistant strains;

the medium CM6 contains: ½MS medium, 0.4~0.6 $\mu mol \cdot L-1$ of NAA, 1.8~2.2 $\mu mol \cdot L-1$ of 6-BA, 28~32 $g \cdot L-1$ of sucrose, and the pH of the medium is 6.0~6.4.

Preferably, in step (1), the mutagenesis power is 140 W, the irradiation distance is 40 mm and the mutagenesis time is 120 s.

Preferably, in step (1), the nitrogen flow is 1.0~1.4 L/min.

More preferably, in step (1), the nitrogen flow is 1.2 L/min.

Preferably, during irradiation mutagenesis in step (1), the applied voltage is 220V.

Preferably, the plasma instrument is an HPD-280 plasma machine produced by Nanjing Suman Electronics Co., Ltd.

Preferably, the plasma instrument is sterilized before use, wherein a vessel containing 28~32% $H_2O_2$ solution is put into a process chamber for diffuse sterilization by vacuum.

Preferably, in step (1), the sugarcane embryonic calli are obtained after 2-3 rounds of subculture.

Preferably, in step (1), the preparation method of the sugarcane embryonic calli is as follows: cutting the tail end of a robust sugarcane plant after its stalk grows out, stripping outer leaves, sterilizing it by alcohol under a sterile condition, and cutting off leaves on the outer layer and both ends thereof, keeping tender leaves 10 mm-50 mm above the growing point and cutting the tender leaves into thin slices, inoculating the slices to a CM1 medium for culturing at 26° C.~28° C. in dark to induce the formation of calli, then subculturing for 1-2 times with a CM1 medium, thus producing the sugarcane embryonic callji.

Preferably, in step (1), the size of the sugarcane embryonic calli is 0.8~1.2 mm×0.8~1.2 mm×0.8~1.2 mm, and the calli are placed in a culture dish side by side, so that each grain of embryonic callus may be irradiated, even the embryonic calli at the bottom of the culture dish may also be discharge irradiated.

Preferably, the CM1 medium is a MS medium containing 1.8~2.2 μmol·L−1 of 2,4-D, 28~32 g·L−1 of sucrose, 7.5~8.5 g·L−1 of agar, and its pH is 6.0~6.4.

Preferably, in step (5), the screening culture is continued for 26~30 d.

Preferably, in step (6), the proliferation culture is continued for 28~32 d.

The present invention will be further described in detail in combination with specific examples.

Example 1

A: Start of the Calli of Superior Cultivated Sugarcane Varieties

1) Preparation of Inoculation Materials

The tail end of a robust sugarcane plant was cut after its stalk grew out, outer leaves were stripped, and sterilization was performed by 75% alcohol for 30 S under a sterile condition. The leaves on the outer layer and both ends of the plant (leaf sheath) were cut off, while the tender leaves 10 mm-50 mm above the growing point were kept and sliced into about 2 mm thin slices ready for inoculation after ½ girdling.

2) Obtainment of Sugarcane Embryonic Calli

The prepared slices were inoculated to a CM1 medium for culturing at 26° C.~28° C. in dark with 6-8 pieces per dish to induce the formation of calli, then subculture was conducted for 1-2 times with a CM1 medium (MS+2.0 μmol·L$^{-1}$ of 2,4-D+30 g·L$^{-1}$ of sucrose+8 g·L$^{-1}$ of agar, pH=6.2) with 6-8 pieces per dish to produce sugarcane embryonic calli.

B: High-Throughput Arrangement

The sugarcane embryonic calli after 2-3 times of subculture ware clipped into about 1 mm×1 mm×1 mm pieces and horizontally laid on the bottom of a culture dish (bottom width 90 mm×height 20 mm), so that each grain of embryonic calli may be irradiated. Then the culture dish was covered by an upper cover and sealed by a polyethylene film for further use.

C: Plasma Parameter Setting

The plasma machine of type HPD-280 produced by Nanjing Suman Electronics Co., Ltd. (marked power on the machine of 40%, 50% and 60% respectively corresponding to the specific power of 140 W, 170 W and 200 W) was used for mutagenesis of sugarcane embryonic calli, with mutagenesis power of 140 W and irradiation distance of 40 mm. The protective gas was nitrogen with the flow of 1.2 L/min. The irradiation mutagenesis time was set to be 120 s and the applied voltage was 220 V.

D: Plasma Operations for Microorganism-Prevention and Mutagenesis

Before treatment, 20 ml 30% $H_2O_2$ contained in a culture dish was first put into a process chamber for diffuse sterilization of the plasma machine by vacuum. Then, the upper cover of the culture dish paved with embryonic calli was removed and the culture dish was placed at the center of the process chamber for irradiation mutagenesis according to the plasma operation instructions. After treatment, the culture dish was covered with the upper cover and sealed by a polyethylene film.

E: Buffering Culture of the Treated Calli

The sugarcane embryonic calli treated by mutagenesis were inoculated to a solid medium CM2 (MS+1.5 μmol·L$^{-1}$ of 2,4-D+30 g L$^{-1}$ of sucrose+8 g·L$^{-1}$ of agar, pH=6.2) and sealed by a polyethylene film for buffering culture for 8~10 days. Meanwhile, statistics was made for the number of survived calli. Survival rate % of embryonic calli=100%× number of survived embryonic calli/number of treated embryonic calli (that is, the survival rate of embryonic calli as shown in the following table 1).

F: Stress Screening

After buffering culture, the sugarcane calli were in turn inoculated to a solid medium CM3 containing 1.5 μmol·L$^{-1}$ of glyphosate and to a solid medium CM3 containing 2.5 μmol·L$^{-1}$ of glyphosate, then sealed by a film for screening culture for 8~10 days;

the medium CM3 containing: a MS medium, 28~32 g·L$^{-1}$ of sucrose and 7.5~8.5 g·L$^{-1}$ of agar, with pH 6.2;

G: Differentiation of Resistant Embryonic Calli to Seedlings

The embryonic calli survived in the above step were selected and transferred to a solid differentiation medium CM4 (MS+0.5 μmol·L$^{-1}$ of NAA+1.0 μmol·L$^{-1}$ of kinetin Kt+50 g·L$^{-1}$ of sucrose+8 g·L$^{-1}$ of agar, pH=6.2) for culture, and were subcultured once after the seedlings emerged.

H: Glyphosate Stress Screening of Bottle Seedlings

After growing to 20 mm-30 mm in the above step, the seedlings were inoculated to a CM5 (MS+5.0 μmol·L$^{-1}$ of glyphosate+30 g·L$^{-1}$ of sucrose+8 g·L$^{-1}$ of agar, pH 6.2) for screening culture for 28 days; controls were inoculated at the same time.

I: Stress Screening Via Spraying Glyphosate on the Leaf Surfaces of Potted Plants The survived seedlings were transferred to a CM4 for proliferation culture for 30 days, and transferred to a CM6 (½MS+0.5 μmol·L$^{-1}$ of NAA+2.0 μmol·L$^{-1}$ of 6-BA+30 g·L$^{-1}$ of sucrose, pH 6.2) for root growth and seedling hardening, then transplanted to a seedbed. When the seedlings grew to 100 mm~150 mm after about 1 month, 5.0 μmol·L$^{-1}$ of glyphosate was sprayed to the leave surfaces once. The finally survived seedlings were glyphosate-resistant strains. Statistics was made for the number of glyphosate-resistant strains. Mutagenesis rate %=100%×number of glyphosate-resistant strains/number of treated embryonic calli*(that is, the mutagenesis rate as shown in the following table 1).

Example 2

On Jul. 15, 2015, an HPD-280 plasma machine was used for mutagenesis of the Yuetang 93-159 sugarcane embryonic calli, with mutagenesis power set to be 140 W and irradiation mutagenesis time of 80 s, 100 s, 120 s, 140 s, 160 s and 180 s respectively. Other operations in Example 2 were the same as those in Example 1. The survival rate and mutagenesis rate of the embryonic calli in each group were measured.

Results of measurement were as shown in table 1, wherein the survival rate of the embryonic calli treated for 120 s was the highest, being 18.3%, which was significantly higher than the other treated groups. Furthermore, embryonic calli of this group can differentiate into plants after two rounds of glyphosate screening with a mutagenesis rate of 2.50%.

TABLE 1

Plasma mutagenesis of the Yuetang 93-159 sugarcane embryonic calli under conditions of power of 140 W and treated time of 80-180 s

| Number of treatment embryonic calli/grain | Power/ W | Mutagenesis time/s | Survival rate of embryonic calli/% | Number of glyphosate-resistant plant/ strain | Mutagenesis rate/% |
|---|---|---|---|---|---|
| 120 | 140 | 80  | 11.7ABab | 2 | 1.67 |
|     |     | 100 | 7.5Bbc   | 1 | 0.83 |
|     |     | 120 | 18.3Aa   | 3 | 2.50 |
|     |     | 140 | 4.2Bc    | 1 | 0.83 |
|     |     | 160 | 3.3Bc    | 1 | 0.83 |
|     |     | 180 | 1.7Bc    | 0 | 0    |

Note: different lowercase English letters behind the data in a same column indicate a significant difference, while different capital English letters indicate an extremely significant difference; same as below;
Survival rate % of embryonic calli = 100% × number of survived embryonic calli/number of treated embryonic calli;
Mutagenesis rate % = 100% × number of glyphosate-resistant strains/number of treated embryonic calli.

Example 3

On May 4, 2016, an HPD-280 plasma machine was used for mutagenesis of the Yuetang 93-159 sugarcane embryonic calli with irradiation mutagenesis time set as 120 s. Mutagenesis power was set to be 140 W, 170 W and 200 W respectively. Other operations in Example 3 were the same as those in Example 1. The survival rate and mutagenesis rate of the embryonic calli in each group were measured.

Results of measurement were as shown in table 2, wherein the survival rate of the embryonic calli treated by power of 140 W was the highest, being 62.4%. After two rounds of glyphosate screening, embryonic calli in each group can differentiate into plants in small number. The power was 140 W when the mutagenesis rate was the highest, being 2.77%.

TABLE 2

Plasma mutagenesis of the Yuetang 93-159 sugarcane embryonic calli under conditions of power 140~200 W and treating time 120 s:

| Number of treatment embryonic calli/grain | treating time/s | treating power/ W | Survival rate of embryonic calli/% | Number of glyphosate-resistant plant/strain | Mutagenesis rate/% |
|---|---|---|---|---|---|
| 180 | 120 | 140 | 62.4a | 5 | 2.77 |
|     |     | 170 | 56.4a | 1 | 0.56 |
|     |     | 200 | 58.3a | 2 | 1.12 |

Example 4

An HPD-280 plasma machine was used for mutagenesis of the Yuetang 93-159 sugarcane embryonic calli, wherein the power was set to be 140 W and callus mutagenesis time was 120 s. These sugarcane embryonic calli were inoculated to a glyphosate solid medium CM2 for buffering culture for 8 d, 10 d and 13 d respectively. Other operations in Example 4 were the same as those in Example 1. The survival rate of the embryonic calli in each group was measured.

Results of measurement were as shown in FIG. 1. It can be seen from the FIG. 1 below that the survival rate of the sugarcane embryonic calli became lower and lower as the number of days of buffering culture increased. Buffering culture time should be 8 d-10 d.

Example 5

Figure 2:
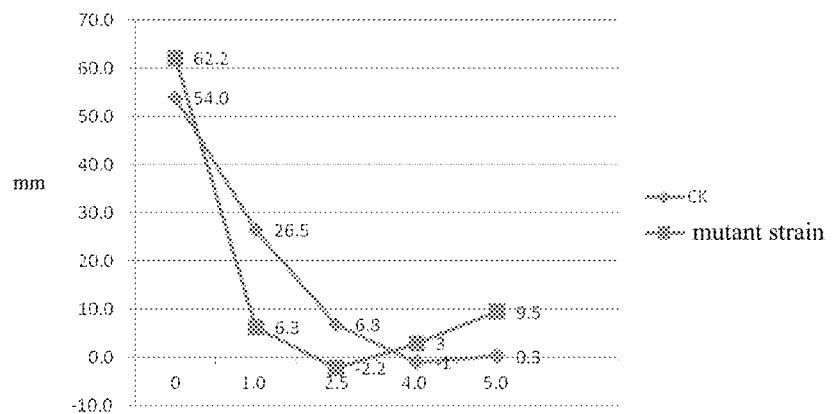
FIG. 2 is a diagram showing the height increments of the glyphosate-resistant strains of the present invention in comparative with those of the plants in the control group (CK) after spraying 0~5.0 $\mu mol \cdot L-1$ of glyphosate.
Figure 3:
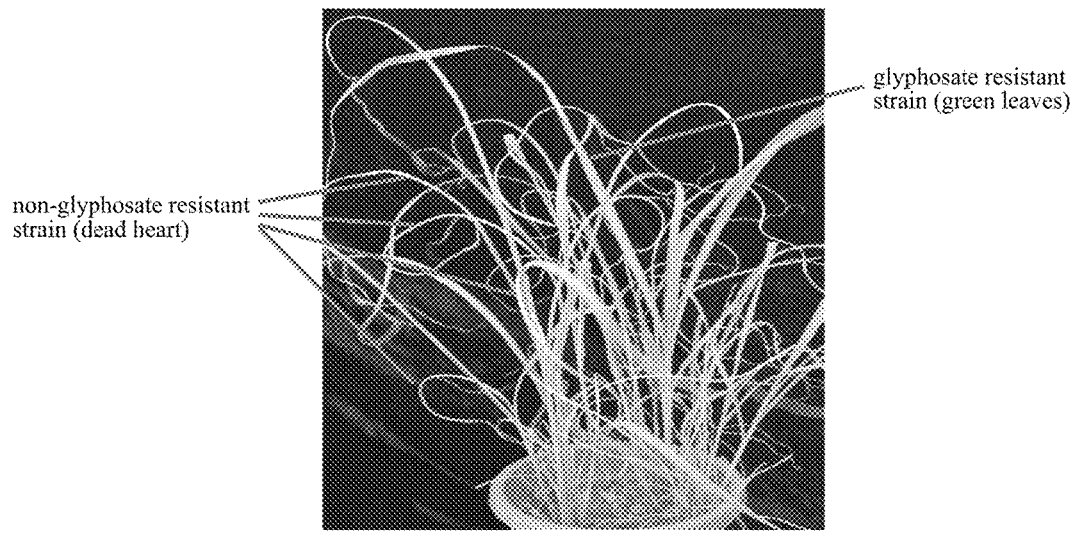
FIG. 3 shows the damage extent with the glyphosate-resistant strains and the non-glyphosate-resistant strains 20 days after spraying 5.0 $\mu mol \cdot L-1$ of glyphosate.
Figure 4:
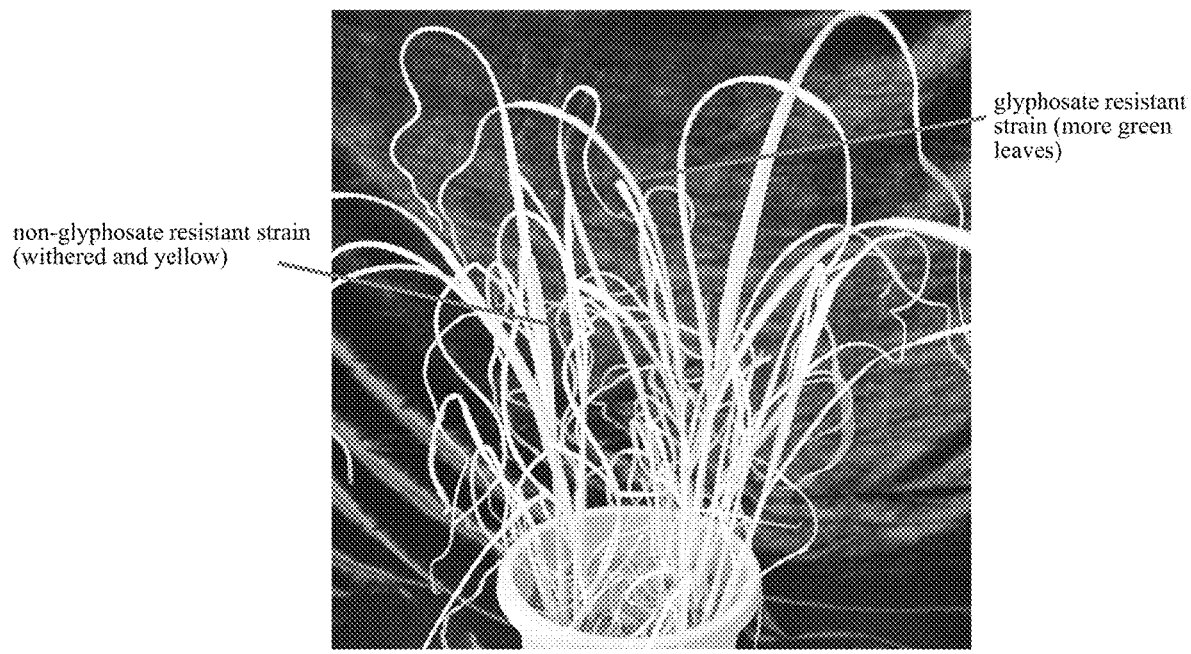
FIG. 4 shows the growing status of the glyphosate-resistant strains and the non-glyphosate-resistant strains 30 days after spraying 5.0 $\mu mol \cdot L-1$ of glyphosate, wherein the left 3 side-by-side strains in the pot are the non-glyphosate-resistant strains and the right 3 side-by-side strains are the mutant strains.

When potted seedlings after mutagenesis grew to 100-150 mm high, 0, 1.0, 2.5, 4.0 and 5.0 µmol·L−1 of glyphosate was sprayed to the leave surfaces respectively. Although the glyphosate-resistant strains were damaged to some extent, these strains may still survive after 20 days. Compared with the control group, the resistant strains had a maximum increment of height, being 9.5 mm (FIG. 2), and still kept green leaves, while plants of the control group suffered rolled leaves in early stage and dead heart in later period (FIG. 3). 30 days later, plants of the control group withered and became yellow, while for the mutant strains, some of the leaves were still green (FIG. 4). It indicated that the mutant strains had strong glyphosate resistance and were glyphosate-resistant strains.

Example 6

An HPD-280 plasma machine was used for mutagenesis of the Yuetang 00-236 sugarcane embryonic calli, wherein the mutagenesis power was set to be 140 W and irradiation mutagenesis time was 120 s. During mutagenesis, the protective gas was set as air, 1.2 L/min of nitrogen and 0.2 L/min of nitrogen respectively. Other operations in Example 6 were the same as those in Example 1.

Results of measurement were as shown in table 3. When 1.2 L/min of nitrogen was adopted as the protective gas, the survival rate of embryonic calli was highest, being 22.2%, which was obviously higher than the other treatment results.

TABLE 3

Influence of different protective gases during mutagenesis on plasma mutagenesis result

| Number of embryonic calli/grain | Mutagenesis time/s | Power/ W | protective gas | Survival rate of embryonic calli/% |
|---|---|---|---|---|
| 180 | 120 | 140 | Air | 13.2a |
|     |     |     | N$_2$ (flow: 1.2 L/min) | 22.2a |
|     |     |     | N$_2$ (flow: 0.2 L/min) | 17.8a |

The above examples are preferred embodiments of the present invention, but embodiments of the present invention are not limited by the above examples, and any other changes, modification, substitution, combination, simplification within the spirit and principle of the present invention shall be regarded as an equivalent displacement of the present invention, and are included within the protection scope of the present invention.

What is claimed is:

1. A method for conducting high-throughput and directed mutagenesis for sugarcane resistance to glyphosate by plasma, comprising the following steps:
    (a) irradiating sugarcane embryonic calli by a plasma instrument under a sterile condition for mutagenesis, wherein the mutagenesis power is 140-200 W, the discharging distance is 35-45 mm, the mutagenesis time is 110-140 s and the protective gas is nitrogen;

(b) inoculating the sugarcane embryonic calli after mutagenesis in the above step in a solid medium CM2 and sealed by a film for buffering culture for 8-10 days;

wherein the medium CM2 contains: a MS medium, 1.2-1.7 µmol·L$^{-1}$ of 2,4-D, 28-32 g·L$^{-1}$ of sucrose and 7.5-8.5 g·L$^{-1}$ of agar, and the pH of the medium is 6.0-6.4;

(c) inoculating the sugarcane calli after buffering culture in a first solid medium CM3 containing 1.2-1.7 µmol·L$^{-1}$ of glyphosate, inoculating in a second solid medium CM3 containing 2.2-2.7 µmol·L$^{-1}$ of glyphosate, then sealing each of the first and second solid medium CM3 with the calli by a film for screening culture for 8-10 days in each of the first and second solid medium CM3;

wherein the medium CM3 contains: a MS medium, 28-32 g·L$^{-1}$ of sucrose and 7.5-8.5 g·L$^{-1}$ of agar, and the pH of the medium is 6.0-6.4;

(d) transferring the embryonic calli survived in the above step to a solid differentiation medium CM4 for culture and conducting subculture after seedlings emerge;

wherein the medium CM4 contains: a MS medium, 0.4-0.6 µmol·L$^{-1}$ of NAA, 0.8-1.2 µmol·L$^{-1}$ of Kt, 48-52 g·L$^{-1}$ of sucrose and 7.5-8.5 g·L$^{-1}$ of agar, and the pH of the medium is 6.0-6.4;

(e) after growing to 20 mm-30 mm, transferring the seedlings in the above step to a medium CM5 for screening culture;

wherein the medium CM5 contains: a MS medium, 4.8-5.2 µmol·L$^{-1}$ of glyphosate, 28-32 g·L$^{-1}$ of sucrose, 8 g·L$^{-1}$ of agar, and the pH of the medium is 6.0-6.4; and (f) inoculating the seedlings survived in the above step in a medium CM4 for proliferation culture, transferring the seedlings to a medium CM6 for root-growth culture and seedling hardening, then transplanting the seedlings to a seedbed; after growing to 100 mm-150 mm, screening the seedlings by spraying 4.8-5.2 µmol·L$^{-1}$ of glyphosate; wherein the survived seedlings are glyphosate-resistant strains; and wherein the medium CM6 contains: ½MS medium, 0.4-0.6 µmol·L$^{-1}$ of NAA, 1.8-2.2 µmol·L$^{-1}$ of 6-BA, 28-32 g·L$^{-1}$ of sucrose, and the pH of the medium is 6.0-6.4.

2. The method according to claim 1, wherein in step (a), the mutagenesis power is 140 W, the irradiation distance is 40 mm and the mutagenesis time is 120 s.

3. The method according to claim 1, wherein in step (a), the nitrogen flow is 1.0-1.4 L/min.

4. The method according to claim 1, wherein the plasma instrument is sterilized before use, wherein a vessel containing 28-32% $H_2O_2$ solution is put into the process chamber in the plasma instrument for diffuse sterilization by vacuum.

5. The method according to claim 1, wherein in step (d), the sugarcane embryonic calli are obtained after 2-3 rounds of subculture.

6. The method according to claim 1, wherein step (a) further comprises the following steps: cutting the tail end of a robust sugarcane plant after its stalk grows out, stripping outer leaves, sterilizing it by alcohol under a sterile condition, cutting off leaves on the outer layer and both ends thereof, keeping tender leaves 10 mm-50 mm above the growing point, cutting the tender leaves into thin slices, inoculating the slices to a medium CM1 for culturing at 26° C.-28° C. in dark to induce the formation of calli, then subculturing for 1-2 times with a medium CM1, thereby producing sugarcane embryonic calli;

wherein the medium CM1 is a MS medium containing 1.8-2.2 µmol·L$^{-1}$ of 2,4-D, 28-32 g·L$^{-1}$ of sucrose, 7.5-8.5 g·L$^{-1}$ of agar, and the pH of the medium is 6.0-6.4.

7. The method according to claim 1, wherein in step (e), the number of days of screening culture is 26-30 d.

8. The method according to claim 1, wherein in step (f), the number of days of proliferation culture is 28-32 d.

\* \* \* \* \*